US00PP20951P2

(12) United States Plant Patent
Ranney

(10) Patent No.: US PP20,951 P2
(45) Date of Patent: Apr. 27, 2010

(54) FLOWERING QUINCE PLANT NAMED 'SCARLET STORM'

(50) Latin Name: *Chaenomeles speciosa*
Varietal Denomination: Scarlet Storm

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/381,214

(22) Filed: Mar. 9, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Jondle & Associates, P.C.

(57) ABSTRACT

'Scarlet Storm' is a new quince plant particularly distinguished by a medium-sized, upright, multi-stemmed, fruitless shrub, large, double-flowers with scarlet-red petals, and thornless stems, is disclosed.

2 Drawing Sheets

Genus and species: *Chaenomeles speciosa.*

Variety denomination: 'Scarlet Storm'.

BACKGROUND OF THE INVENTION

The present invention comprises a new and distinct cultivar of flowering quince, botanically known as *Chaenomeles speciosa,* and hereinafter referred to by the cultivar name 'Scarlet Storm'. This new flowering quince was developed through a breeding program at North Carolina State University, Mills River, N.C. 'Scarlet Storm' is an $F_1$ hybrid between the female parent, *Chaenomeles speciosa* 'Spitfire' (unpatented) and the male parent, *Chaenomeles speciosa* 'Dragons Blood' (unpatented). The first asexual propagation of 'Scarlet Storm' was carried out in June 2003 by rooting stem cuttings at the North Carolina State University, Mountain Horticultural Crops Research Station, Mills River, N.C. and has been asexually reproduced repeatedly by vegetative cuttings in North Carolina over a five year period.

'Scarlet Storm' roots readily from softwood cuttings treated with a basal dip of 5,000 ppm indole butyric acid (potassium salt) in water. 'Scarlet Storm' has been found to retain its distinctive characteristics through successive asexual propagations.

Plant Breeder's Rights for this cultivar have not been applied for. 'Scarlet Storm' has not been made publicly available more than one year prior to the filing date of this application.

SUMMARY OF THE INVENTION

The following are the most outstanding and distinguishing characteristics of this new cultivar when grown under normal horticultural practices at North Carolina State University, Mountain Horticultural Crops Research Station, Mills River, N.C.

1. A medium-sized, upright, multi-stemmed, fruitless shrub;
2. Large, double-flowers with scarlet-red petals; and
3. Thornless stems.

DESCRIPTION OF THE PHOTOGRAPHS

This new quince plant is illustrated by the accompanying photographs which show the plant's form, foliage and inflorescences. The colors shown are as true as can be reasonably obtained by conventional photographic procedures. The photographs were taken on Apr. 10, 2008 on 2-year-old plants, growing under field conditions in Mills River, N.C.

DESCRIPTION OF THE NEW CULTIVAR

Figure 1:
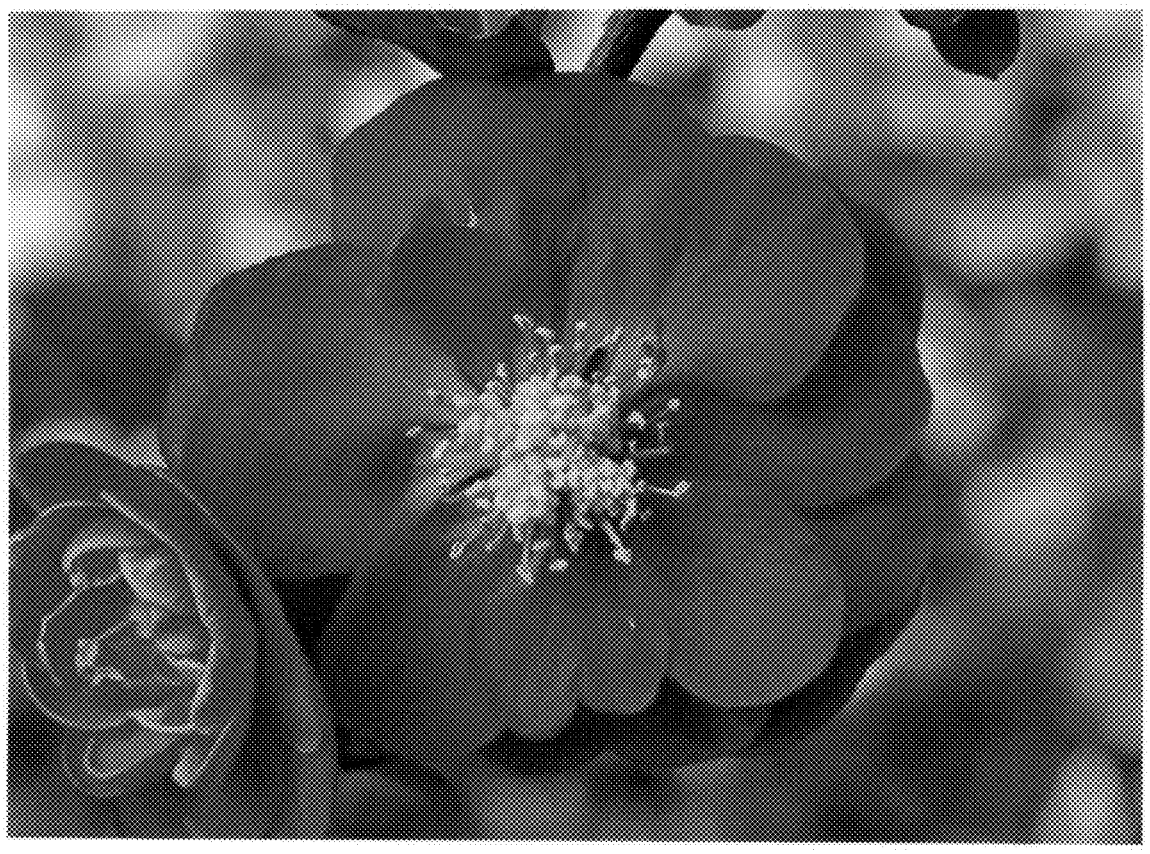
FIG. 1 shows a close-up of the large, scarlet-red, double flower, lacking a pistil.
Figure 2:
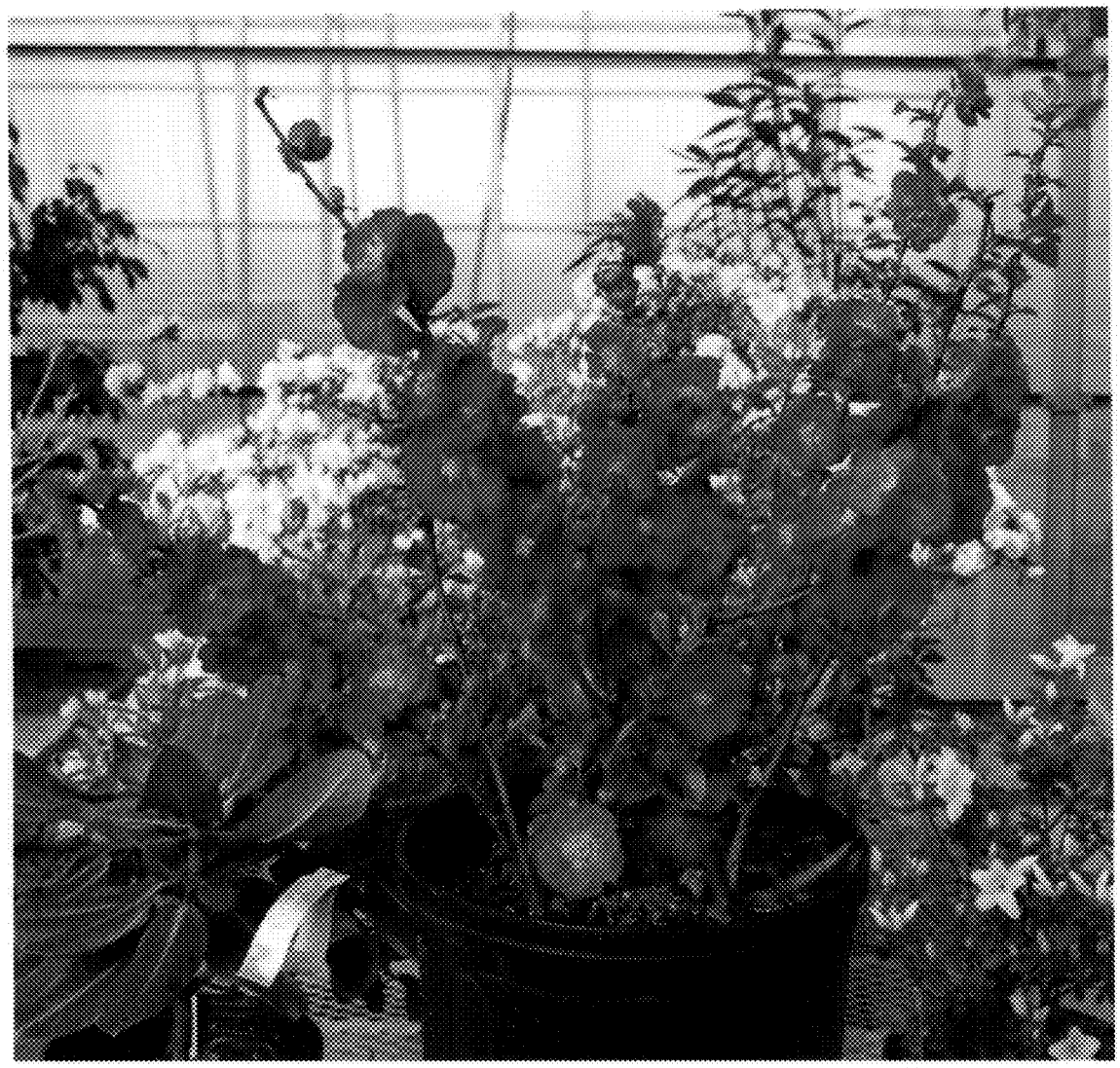
FIG. 2 shows a 2-year old container-grown plant in full-bloom.

The following detailed description sets forth the distinctive characteristics of 'Scarlet Storm'. The detailed description was taken on 7-year-old plants growing under landscape conditions in Mills River, N.C. in April 2008. Color references are to The R.H.S. Colour Chart of The Royal Horticultural Society of London (R.H.S.), 2001 Edition.

DETAILED BOTANICAL DESCRIPTION

Classification:
- *Botanical name.*—*Chaenomeles speciosa.*
- *Common name.*—Quince.

Parentage:
- *Female parent.*—*Chaenomeles speciosa* 'Spitfire' (unpatented).
- *Male parent.*—*Chaenomeles speciosa* 'Dragons Blood' (unpatented).

Plant description:
- *Growth habit.*—Upright.
- *Plant shape.*—Globose.
- *Height at maturity.*—2 meters to 3.33 meters.
- *Width at maturity.*—2 meters to 3.33 meters.

Stem:
- *Mature stem color.*—RHS N199B (Grey-brown).
- *Immature stem color.*—Ranging from and including RHS 152C (Yellow-green) to RHS N199C (Grey-brown).
- *Quantity of thorns.*—Thorns are absent.

Leaves:

*Type.*—Deciduous.

*Arrangement.*—Alternate.

*Shape.*—Elliptic.

*Apex.*—Rounded to acute.

*Base.*—Attenuate.

*Margin.*—Serrulate.

*Mature leaf size.*—Length: Average is 6.71 cm (range is 5.41 cm to 8.0 cm). Width: Average is 3.92 cm (range is 3.44 cm to 4.4 cm).

*Immature leaf color.*—Adaxial (upper) surface: RHS 146A (Yellow-green) with some RHS 46A (Red) highlights. Abaxial (lower) surface: RHS 146C (Yellow-green) with some RHS 46A (Red) highlights.

*Mature leaf color.*—Adaxial (upper) surface: RHS 137A (Green). Abaxial (lower) surface: RHS 148B (Yellow-green).

*Stipule.*—Color: Adaxial (upper) surface: RHS 137A (Green). Abaxial (lower) surface: RHS 148B (Yellow-green). Size (fully-expanded): Length: Average is 1.0 cm (range is 0.76 cm to 1.23 cm). Width: Average is 1.75 cm (range is 1.61 cm to 1.89 cm).

*Leaf attachment.*—Petiolate.

*Petiole.*—Shape: Laterally compressed. Length: Average is 0.41 cm (range is 0.35 cm to 0.5 cm). Width: Average is 0.11 cm (range is 0.1 cm to 0.12 cm). Surface: Glabrous (not pubescent).

Flower:

*Number of flowers per cluster.*—2 to 4.

*Type.*—Double flower.

*Habit.*—Seasonal (spring).

*Flowering season.*—Early spring through late spring.

*Lastingness of flower on the plant.*—7 to 21 days.

*Fragrance.*—Absent.

*Diameter at anthesis.*—Average is 5.5 cm (range is 4.7 cm to 6.5 cm).

*Self cleaning or persistent.*—Self-cleaning.

*Petal.*—Number of petals per flower: Average is 22 (range is 17 to 25). Color, adaxial (upper) surface at anthesis: RHS 45A to RHS 47A (Red). Color, abaxial (lower) surface: As the flower expands (pre-anthesis), color is RHS 46B (Red) and at anthesis, color is RHS 45A to RHS 46B (Red). Surface texture (on both surfaces) and appearance: Glabrous (not pubescent) to lustrous (shiny). Shape: Flabellate. Apex: Rounded. Base: Cuneate. Margin: Entire. Length: Average is 2.36 cm (range is 1.29 cm to 2.87 cm). Width: Average is 1.57 cm (range is 0.51 cm to 2.37 cm). Petals, fused or unfused: Unfused.

*Peduncle.*—Shape: Cylindrical. Length: Average is 0.89 cm (range is 0.35 cm to 1.4 cm). Width: Average is 0.1 cm (range is 0.05 cm to 0.15 cm). Color: Closest to RHS 143D (Green). Surface texture: Glabrous (not pubescent).

Calyx/receptacle:

*Shape and arrangement.*—5-lobed and globular to globular conical.

*Calyx/receptacle size.*—Length: Average is 1.44 cm (range is 1.33 cm to 1.57 cm). Width: Average is 1.53 cm (range is 1.34 cm to 1.61 cm). Depth: Average is 0.45 cm (range is 0.32 cm to 0.78 cm).

*Lobe number.*—5.

*Lobe apex.*—Truncate.

*Lobe base.*—Fused.

*Lobe margin.*—Ciliate.

*Lobe length.*—Average is 0.9 cm (range is 0.8 cm to 1.0 cm).

*Lobe width.*—Average is 0.65 cm (range is 0.55 cm to 0.75 cm).

*Lobe color, adaxial (upper) surfaces.*—RHS 46A (Red) and RHS 143D (Green).

*Lobe color, abaxial (lower) surfaces.*—RHS 143D (Green) and RHS 46A (Red) at the margins.

*Lobe surface texture, adaxial (upper) surface.*—Glabrous (not pubescent).

*Lobe surface texture, abaxial (lower) surface.*—Pubescent.

Reproductive organs:

*Stamen.*—Quantity per flower: Average is 144 (range is 58 to 188). Shape: Filament. Color: RHS 150D (Yellow-green) at anthesis. Attachment: Dorsifixed. Length: Average is 0.6 cm (range is 0.6 cm to 1.2 cm). Width: Less than 0.05 cm. Anther: Length: Average is 0.18 cm (range is 0.1 cm to 0.275 cm). Width: Average is 0.125 cm (range is 0.1 cm to 0.15 cm). Shape: Ovoid. Color: Typically RHS 12C (Yellow) but ranges from RHS 8A to RHS 12C. Pollen color: RHS 12C (Yellow). Pollen amount: Moderate.

*Pistil.*—Absent.

*Ovary.*—Absent.

Fruit/seed set: None observed.

Disease and insect resistance: No significant disease or insect pests have been observed.

COMPARISON WITH PARENTAL LINES AND KNOWN CULTIVARS

'Scarlet Storm' is distinguished from the female parent, *Chaenomeles speciosa* 'Spitfire' (unpatented) in that 'Scarlet Storm' has 17–25 petals, flowers without pistils, is thornless and lacks fruit, while 'Spitfire' has 5 petals, flowers with pistils, has some thorns on the stems and produces fruit.

'Scarlet Storm' is distinguished from the male parent, *Chaenomeles speciosa* 'Dragons Blood' (unpatented) in that 'Dragons Blood' generally has fewer and smaller (less than 5 cm in diameter) flowers.

Table 1 shows the differences between 'Scarlet Storm' and commercial varieties 'Jet Trail' (unpatented) and 'Toyo-Nishiki' (unpatented).

TABLE 1

COMPARSION TO COMMERCIAL CULTIVARS

| | Cultivar | | |
|---|---|---|---|
| Trait | 'Scarlet Storm' | 'Jet Trail' | 'Toyo-Nishiki' |
| Flower Color | Scarlet red, RHS 45A to RHS 47A | White, RHS N155 | Emerges White, RHS N155; Fading to Pink, RHS 49A to RHS 51C |
| Petal Number/Flower | 17 to 25 | 5 to 6 | 5 |
| Flower Diameter | 4.8 cm to 6.0 cm | 5.0 cm to 6.0 cm | 3.0 cm to 5.6 cm |
| Pistil | Lacking | Present | Generally Present |
| Fruit | Lacking | Present | Present |
| Thorns | Lacking | Lacking | Present |

I claim:

1. A new and distinct cultivar of quince plant as shown and described herein.

* * * * *